United States Patent [19]

Bauer

[11] 4,262,092

[45] Apr. 14, 1981

[54] PROCESS FOR PRODUCING N-ACYL-D-PHENYLALANINE ESTER

[75] Inventor: Dennis P. Bauer, Baton Rouge, La.

[73] Assignee: Ethyl Corporation, Richmond, Va.

[21] Appl. No.: 37,162

[22] Filed: May 8, 1979

[51] Int. Cl.$^3$ .............................................. C07B 19/02
[52] U.S. Cl. ................................... 435/280; 435/222; 435/225
[58] Field of Search .......................................... 435/280

[56] References Cited

U.S. PATENT DOCUMENTS

| | | | |
|---|---|---|---|
| 3,031,380 | 4/1962 | Minagawa et al. | 435/172 |
| 3,347,752 | 10/1967 | Ravenbusch et al. | 435/280 |
| 3,813,317 | 5/1974 | Benoiton et al. | 435/280 |
| 3,907,638 | 9/1975 | Uzuki et al. | 435/280 |
| 3,963,573 | 6/1976 | Stauffer | 435/280 |

FOREIGN PATENT DOCUMENTS 855051 11/1977 Belgium .

OTHER PUBLICATIONS

Guntelberg et al., C. R. Trav. Lab. Carlsberg, Ser. Chim 29, 36 (1954).
Subromanian et al., Biochemistry, vol. 3, No. 12, pp. 1861-1874, (1964).
Smith et al., Journal of Biological Chemistry, vol. 241, No. 24, pp. 5974-5976, (1966).
Narahoshi et al., Journal of Biochemistry, vol. 62, No. 6, pp. 633-641, (1967).
Danno et al., Ag. Biol. Chem., vol. 31, No. 10, pp. 1151-1158, (1967).
Barel et al., Journal of Biological Chemistry, vol. 243, No. 7, pp. 1344-1348, (1968).
Misaki et al., Agr. Biol. Chem., vol. 34, No. 9, pp. 1383-1392, (1970).
Kareko et al., Synthetic Production and Utilization of Amino Acids, J. Wiley & Sons, pp. 171-179, (1974).

Primary Examiner—Alvin E. Tanenholtz
Attorney, Agent, or Firm—Donald L. Johnson; John F. Sieberth; James M. Pelton

[57] ABSTRACT

Production of optically pure N-acyl-D-phenylalanine ester by reacting a racemic mixture of N-acyl-D,L-phenylalanine ester with a proteolytic enzyme and separating the resulting N-acyl-D-phenylalanine ester from the solution with subsequent removal of the N-acyl and ester groups to provide D-phenylalanine.

9 Claims, No Drawings

PROCESS FOR PRODUCING N-ACYL-D-PHENYLALANINE ESTER

BACKGROUND OF THE INVENTION

This invention relates to a process for producing N-acyl-D-phenylalanine esters.

Heretofore, the resolution of racemic D,L-phenylalanine mixtures has followed three different routes of optical resolution in order to obtain one of the optically active antipodes. The first includes asymmetric hydrolysis of N-chloroacetyl-D,L-phenylalanine by the carboxypeptidase in pancrease. A second involves asymmetric hydrolysis of N-acetyl-D,L-phenylalanine by mould aminoacylase which process can be operated in a continuous fashion using a packed column. And, finally, a physico-chemical resolution based on preferential crystallization of isomers from supersaturated solution of acetyl-D,L-phenylalanine ammonium salt. In addition, there are several synthetic methods for production of L-phenylalanine. For example, conversion of L-tyrosine, treatment of synthetic phenylpyruvic acid with transaminase and enzymatic isomerization of synthetic D,L-phenylalanine by microorganisms. Kaneko et al, *Synthetic Production and Utilization of Amino Acids*, J. Wiley & Sons, pp. 171–179 (1974).

In Belgian Patent 855,051, there is taught a method and a composition for treatment of D,L-amino acids to resolve the racemic mixture and obtain L-isomer in which a supported aminoacylase is used to treat aqueous solutions of the D,L-amino acid. The support is a porous inorganic substrate of specified grain size, surface area, pore diameter and volume and is coated with a network polymer film, or carries a tertiary amine or a quaternary ammonium salt group. Typical supports are titania, alumina or silica. The network polymer can be polyamino epoxides, polyamineformaldehyde, phenolformaldehyde mixtures and polymerized mixtures of vinyl monomers. The aminoacylases are enzymes of animal orgin, such a pork kidney extracts or microorganism products, such as from Aspergillus, *Lactobacillus arabinosus, Micrococcus glutamicus*, and *Pseudomonoas cruciviae*. The process includes contacting the amino acids, such as N-acetyl-D,L-amino acid, with the complex of support/tertiary amine/polymer network/enzyme, for example, by passing through a packed column.

In U.S. Pat. No. 3,963,573, there is taught a process for producing optically pure N-acyl-L-methionine by subjecting an N-acyl-D,L-methionine ester to the action of a proteolytic enzyme selected from the group consisting of sulfhydryl proteinases and microbially derived serine proteinases and separating the resulting N-acyl-L-methionine. The art has recognized that certain proteolytic enzymes can be produced in a pure foam, such as from *Bacillus subtilis*, Guntelberg *Trav. Lab. Carlsberg*, Ser. Chim. Vol. 29, p. 36 (1954). The proteolytic enzyme prepared from the strain of *Bacillus subtilis* was purified by crystallization and its physico-chemical properties were determined. The enzymatic properties were investigated insofar as optimum pH for milk coagulation, stability, degradation of casein, hydrolysis of hemoglobin, activators and inhibitors for the enzymes, the effect on ovalbumin and other characteristics. In the *Journal of Biological Chemistry*, Vol. 243, No. 7, pp. 1344–1348 (1968), Barel, examined the activity of Carlsberg and Novo subtilisins toward a number of N-acetylamino acid esters and amino acid esters. The enzymes were also compared with respect to their efficiency in catalyzing aminolysis reactions, their rates of inactivation by certain aromatic sulfonyl halides and the rates of deacylation of their N-trans-cinnamoyl derivatives. Although the enzymes were found qualitatively indistinguishable from the standpoint of substrate specifity, significant quantitative differences were observed. Thus, the microbially derived serine proteinases, for example, Novo and Carlsberg subtilisin exhibited varying of degrees of esterase activity on various N-acyl-L-amino acid esters. However, there is not disclosed a process for resolution of N-acyl-D,L-phenylalanine esters employing the activity of serine proteinases.

D-phenylalanine heretofore had little, if any, use. However, it has recently been found that D-phenylalanine is a simple non-addictive analgesic compound that stimulates the body's own pain-fighting system, provides significant relief in cronic-pain patients and produced long term analgesia. Therefore, a process for producing N-acyl-D-phenylalanise esters and, particularly, N-$C_{1-9}$ acyl-D-phenylalanine esters which can be converted easily to D-phenylalanine would be very desirable. An especially effective process would involve (1) readily available and inexpensive material, such as enzyme, and (2) produce high purity material in high yield at a rapid rate.

SUMMARY OF THE INVENTION

This invention provides an especially effective process for obtaining N-$C_{1-9}$ acyl-D-phenylalanine ester which can be subsequently converted to D-phenylalanine. In one aspect of this invention, there is provided a process for producing optically pure N-acyl-D-phenylalanine ester, comprising:

(a) subjecting a mixture N-acyl-D-phenylalanine ester and N-acyl-L-phenylalanine ester to the action of a proteolytic enzyme selected from the group consisting of microbially derived serine proteinases; and (b) separating the resulting N-acyl-L-phenylalanine from the unreacted N-acyl-D-phenylalanine ester.

In another aspect, this invention involves a process for preparing optically pure N-acetyl-D-phenylalanine ester comprising:

(a) subjecting an aqueous solution of a mixture of N-acetyl-D-phenylalanine methyl ester and N-acetyl-L-phenylalanine methyl ester to the action of a proteolytic enzyme which is a member selected from the group consisting of the microbially derived serine proteinases, at a pH in the range of from 5 to 10;

(b) separating the resulting N-acetyl-L-phenylalanine from the unreacted N-acetyl-D-phenylalanine ester; and (c) recovering the N-acetyl-D-phenylalanine ester.

DETAILED DESCRIPTION OF PREFERRED EMBODIMENTS

As indicated above, this invention relates to a process for producing optically pure N-acyl-D-phenylalanine esters comprising:

(a) subjecting N-acyl-D,L-phenylalanine ester to the action of a proteolytic enzyme selected from the group consisting of microbially derived serine proteinases; and (b) separating the unreacted N-acyl-D-phenylalanine ester from the resulting N-acyl-L-phenylalanine.

As used herein, "optically pure N-acyl-D-phenylalanine ester" means N-acyl-D-phenylalanine ester substantially free of the L-isomer.

It has been found that certain readily available proteinases, namely, microbially derived serine proteinases exhibit high esterase activity for N-acyl-L-phenylanine esters. Furthermore, it has been found that the high esterase activity exhibited for the L-isomer is not inhibited by the presence of the D-isomer. Subjecting N-acyl-D,L-phenylalanine ester to the action of such a proteinase provides a mixture of N-acyl-D-phenylalanine ester and N-acyl-L-phenylalanine. The N-acyl-L-phenylalanine can be readily separated from the mixture by conventional means, for example, by adjusting the pH of an aqueous mixture thereof and extracting with an organic solvent such as chloroform, ethyl acetate, butyl acetate, methylene chloride and the like.

A variety of specific N-acyl-D,L-phenylalanine ester mixtures can be employed in this invention. Preferably, compounds will have the acyl and ester groups mentioned hereinbelow.

Preferably, the acyl group is derived from fatty acids containing from 1 to 9 carbon atoms. More particularly, the N-acyl group will preferably be formyl, acetyl, propionoyl, butyroyl, valeroyl, caproyl, enanthoyl, capryryl, or pelargonoyl. The ester group can be derived from a variety of alchols containing from 1 to 10, preferably from 1 to 6, carbon atoms. Especially suitable examples of ester groups are methyl, ethyl, n-propyl, isopropyl, n-butyl, sec. butyl and isobutyl. Especially suitable examples of acyl groups are formyl, acetyl and propionyl. Racemic N-acetyl-D,L-phenylalanine methyl ester is most preferred for use in the process of this invention.

Serine proteinases suitable for use in this invention are derived from microorganisms such as bacteria, fungi and mold. Microbially derived serine proteinases are preferred for use in the process of this invention. These proteinases are relatively inexpensive and commercially available.

An example of preferred serine proteinases for use in this invention are those derived from the bacterial organism *Bacillus subtilis* and termed subtilisins.

A preferred subtilisin of the present invention is the *Bacillus subtilis*-derived Carlsberg strain. The Carlsberg strain employed in accordance with the present invention is a known subtilisin strain, the amino acid sequence of which is described in Smith et al, "The Complete Amino Acid Sequence of Two Types of Subtilisin, BPN' and Carlsberg, "*J. of Biol. Chem.*, Vol. 241, Dec. 25, 1966, at Page 5974. This subtilisin strain is characterized by a tyrosine to tryptophan ratio of about 13:1. The above reference including its description of the amino acid sequence of the Carlsberg subtilisin is hereby incorporated by reference.

An X-ray mutated *Bacillus subtilis*-derived subtilisin constitutes another preferred subtilisin of the present invention. This mutation can be effected in accordance with U.S. Pat. No. 3,031,380, issued Apr. 24, 1962, to Minagawa et al by irradiation of a *Bacillus subtilis* organism with X-rays. Subsequent treatment in a conventional manner can be employed to result in the preparation of an enzymatic composition. The patent describes a process whereby an enzymatic composition is produced by subjecting *Bacillus subtilis* to X-rays of an intensity corresponding substantially to 24–50 roentgens for an interval of at least half an hour, selecting from the colony thus subject to X-rays a strain identified by cells having hairless, rough, jagged, spotted and dull white characteristics, separating said strain and placing the separated strain in a culture selected from the group consisting of wheat bran and corn meal, maintaining the culture for a period of at least 40 hours while aerating the culture substantially continuously, and drying the culture. The disclosure of U.S. Pat. No. 3,031,380 is hereby incorporated by reference.

Other examples of suitable serine proteinases for use herein include the following. Serine proteinases derived from *Aspergillus oryzae*. Methods for producing and separating these mold derived enzymes are known to those skilled in the art. See, for example, Subramamian et al, *Biochemistry*, Vol. 3, No. 12, Pages 1861–74 (1964), and Misaki et al, *Agr. Biol. Chem.*, Vol. 34, No. 9, Pages 1383–92 (1970). Serine proteinase derived from *Streptomyces griseus* (ATCC 3463). Such serine proteinases are available commercially under the tradename "Pronase" from Kaken Chemical Co., Japan. Methods for producing and separating the proteinases are known. See, for example, Narahashi et al, *The Journal of Biochemistry*, Vol. 62, No. 6, Pages 633–41 (1967). Serine proteinase derived from *Aspergillus sydowi*. Methods for producing and separating this fungally derived serine proteinase are known. See, for example, Danno et al, *Agr. Biol. Chem.*, Vol. 31, No. 10, Pages 1151–58 (1967).

Other suitable examples of microbially derived serine proteinases are Aspergillus alkaline proteinase (E. C. 3.4.21.15), Alternaria endopeptidase (E. C. 3.4.21.16), Arthrobacter serine proteinase (E. C. 3.4.21.17). These particular enzymes have been identified according to a systematic nomenclature involving an "E. C. number". See "Enzyme Nomenclature", Commission of Biochemical Nomenclature, Elsevier Publishing Company (1973), U.S. Library of Congress Card No. 73-78247.

The action of the proteolytic enzyme of the N-acyl-D,L-phenylalanine ester is very suitably conducted in an aqueous medium maintained at a pH of from about 5 to about 10, preferably from about 7 to about 8, and at a temperature of from about 10° to about 60° C. Preferably, the temperature is maintained in the range of from about 20° to about 40° C.

Because of the high selective esterase activity of the particular proteolytic enzymes employed in this invention toward N-acyl-L-phenylalanine ester in N-acyl-D,L-phenylalanine ester mixtures very small amounts of the proteolytic enzyme are required in order to rapidly produce N-acyl-L-phenylalanine and separate it from N-acyl-D-phenylalanine ester. For example, aqueous solutions containing from about 0.0005% to about 1.0%, by weight, preferably from about 0.005% to about 0.5%, by weight, of enzymes are employed. The amounts of enzyme referred to herein refer to pure crystalline enzyme.

The amount of N-acyl-D,L-phenylalanine ester employed will generally be at least about 5%, by weight, of the aqueous solution. Preferably, larger amounts are employed, for example, amounts up to and exceeding the maximum solubility of the N-acyl-D,L-phenylalanine ester in the aqueous medium. Preferably, about 10 weight percent of N-acyl-D,L-phenylalanine ester in the aqueous solution is preferred. Amounts slightly exceeding the maximum solubility can be employed since as the L-isomer is consumed by the action of the enzyme more will enter solution.

The rate of the action of the enzyme on the material will depend on the concentration of the enzyme and ester in solution. In this regard, N-acetyl-D,L-phenylalanine methyl ester is quite suitable in that it exhibits good solubility in water (about 20% by weight at pH 7.5 and 25° C.). Therefore, N-acetyl-D,L-phenylalanine methyl ester is a preferred ester substrate of this invention and a detailed specific embodiment of the invention employing this material is provided in the following example.

EXAMPLE

Part A. Preparation of N-acetyl-D,L-phenylalanine methyl ester

Into a 100 milliliter round bottom flask were placed 10.36 grams (50 millimoles) of N-acetyl-D,L-phenylalanine, 48 grams (1.5 moles) of methanol and 2 grams of sulfuric acid (0.02 moles). The mixture was refluxed for 3 hours. The solvent was then removed under vacuum and the resulting oily residue was taken up in 100 milliliters of ether, washed with 50 milliliters of 5% sodium bicarbonate, 50 milliliters of saturated sodium chloride solution, dried over magnesium sulfate, filtered and the solvent removed under water aspirator vacuum to leave an oily residue. The oily residue was titurated with 100 milliliters of petroleum ether and then the petroleum ether was removed with a water aspirator. The oily residue was vacuum dried in 3 minutes. The white mass was broken up and washed with additional petroleum ether, filtered and vacuum dried. Yield of the white product, N-acetyl-D,L-phenylalanine methyl ester, was 75%. The melting point was 62°–64°. The proton NMR and infrared spectra agreed with the conclusion that the methyl ester of N-acetyl-D,L-phenylalanine was prepared.

Part B. Separation of N-acetyl-D-phenylalanine methyl ester

Into a 100 milliliter beaker were placed 2.21 grams (10 millimoles) of N-acetyl-D,L-phenylalanine methyl ester and 19.91 grams of water. The slurry was adjusted to pH 7.5 with 0.2 N sodium hydroxide. Then, 0.01 grams (0.05 wt % based on the aqueous solution) of purified Carlsberg subtilisn, a serine proteinase commercially available under the tradename "Alcalase" from Novo Industries, Copenhagen, Denmark, was added with stirring. The pH of the solution immediately decreased and was readjusted to pH 7.5 and maintained thereat until enzyme activity ceased after about 46 minutes. A total of 24.3 milliliters of 0.2 N sodium hydroxide was delivered.

The reaction mixture was extracted twice with 100 milliliters of methylene chloride. The organic extracts were combined, dried and solvent removed under vacuum to yield 1.08 grams of N-acetyl-D-phenylalanine methyl ester. The yield was 97.6%, proton NMR confirmed the structure. The optical purity obtained was 98%.

The aqueous layer from the extracts was acidified to a pH of 1 by dropwise addition of concentrated sulfuric acid. It was then extracted twice with 100 milliliter portions of ethyl acetate. The organic extracts were combined, dried and solvent removed under vacuum to yield 1 gram of N-acetyl-L-phenylalanine for 96.5% yield. Proton NMR confirmed the structure and the optical purity was greater than 98% of N-acetyl-L-phenylalanine.

Thus, the racemic solution can be separated and substantially pure N-acetyl-D-phenylalanine methyl ester can be obtained. This example represents the comprehensive procedure for obtaining optically pure N-acetyl-D-phenylalanine methyl ester. It should be understood by a skilled artisan that a variety of methods are available for forming N-acyl-D,L-phenylalanine esters and a variety of methods are also available for separating mixtures of N-acyl-D-phenylalanine esters and N-acyl-L-phenylalanine.

The foregoing example can be repeated employing serine proteinases such as subtilisin BPN, BPN' or *Aspergillus oryzae* derived proteinase with similar results. Further, the D,L ester material can be methyl, ethyl, propyl, or isopropyl esters of N-formyl-D,L-phenylalanine; ethyl, propyl or isopropyl esters of N-acetyl-D,L-phenylalanine; a methyl, ethyl, propyl or isopropyl ester of N-propionyl-D,L-phenylalanine. Similar results are obtained in production of optically pure N-(formyl, acetyl or propionyl-D-phenylalanine esters) which can be separated from the N-(formyl, acetyl or propionyl)-L-phenylalanine.

The N-acyl-D-phenylalanine ester provided by the process of this invention can be converted to D-phenylalanine in a simple procedure. In one procedure, it can be treated at elevated temperatures with dilute acid; for example, it can be dissolved in 2 N HBr and this solution warmed for a time at 80°–100° C. Other simple hydrolysis procedures can be employed to convert the N-acyl-D-phenylalanine esters into the desired D-phenylalanine.

D-phenylalanine has recently been determined to provide significant analgesic action. It is believed to work by inhibiting enzymes responsible for destroying naturally produced, short-acting pain killers. Specifically, D-phenylalanine has been found to be an inhibitor of carboxypeptidase A, and is useful in preventing such enzymes from breaking down enkephalins which are natural analgesics. Tests have shown marked long term analgesia using D-phenylalanine as an investigational new drug.

Having described the invention, it is recognized that skilled artisans will recognize many variations within the scope and spirit of the invention. Therefore, it is desired that the invention be limited only by the lawful scope of the following claims.

What is claimed is:

1. A process for producing optically pure N-acyl-D-phenylalanine ester comprising:
   (a) subjecting a mixture of N-acyl-D-phenylalanine ester and N-acyl-L-phenylalanine ester to the action of a proteolytic enzyme selected from the group consisting of microbially derived serine proteinases; and
   (b) separating the unreacted N-acyl-D-phenylalanine ester from the resulting N-acyl-L-phenylalanine.

2. The process of claim 1 wherein the acyl group contains from 1–9 carbon atoms.

3. The process of claim 2 wherein the ester group contains from 1–10 carbon atoms.

4. The process of claim 1 wherein the proteolytic enzyme is a microbially derived serine proteinase which is a member selected from the group consisting of subtilisin Carlsberg and subtilisin BPN.

5. The process of claim 1 wherein the mixture of N-acyl-L-phenylalanine ester and N-acyl-D-phenylalanine ester comprises N-acetyl-D,L-phenylalanine methyl ester.

6. The process according to claim 1 for preparing optically pure N-acetyl-D-phenylalanine ester comprising:
(a) subjecting an aqueous solution of a mixture of N-acetyl-D-phenylalanine methyl ester and N-acetyl-L-phenylalanine methyl ester to the action of a proteolytic enzyme selected from the group consisting of microbially derived serine proteinases at a pH in the range of from 5 to 10;
(b) separating the unreacted N-acetyl-D-phenylalanine ester from the resulting N-acetyl-L-phenylalanine; and
(c) recovering the N-acetyl-D-phenylalanine ester.

7. The process according to claim 6 which is carried out at a pH in the range from about 5 to about 7.5 and at a temperature in the range from about 10° C. to about 60° C.

8. The process according to claim 7 wherein the entire proteinase is a member selected from the group consisting of subtilisin Carlsberg and subtilisin BPN.

9. The process according to claim 8 wherein the proteinase is subtilisin Carlsberg and the temperature is in the range from about 20° C. to about 40° C.

UNITED STATES PATENT AND TRADEMARK OFFICE
CERTIFICATE OF CORRECTION

PATENT NO. : 4,262,092
DATED : April 14, 1981
INVENTOR(S) : Dennis Paul Bauer

It is certified that error appears in the above–identified patent and that said Letters Patent are hereby corrected as shown below:

Column 1, line 41, reads "such a", should read -- such as --; line 56, reads "foam", should read -- form --. Column 2, line 7, reads "specifity", should read -- specificity --. Column 3, line 29, reads "alchols", should read -- alcohols --. Claim 8, line 2, reads "entire proteinase", should read -- serine proteinase --.

Signed and Sealed this

Twenty-first Day of July 1981

[SEAL]

Attest:

GERALD J. MOSSINGHOFF

Attesting Officer

Commissioner of Patents and Trademarks